United States Patent [19]
Castagner et al.

[11] Patent Number: 5,913,252
[45] Date of Patent: Jun. 15, 1999

[54] PYROTECHNIC TOOL DRIVING DEVICE

[75] Inventors: Bernard Castagner, 4 Chemin de Bourgogne, 77700 Coupvray; Jean Pierre Boyault, Lognes; Dominique Dufaut, Esbly; Alain Nguyen, Roissy-en-Brie; Claude Waitzenegger, Noisy-le-Roi, all of France

[73] Assignee: Bernard Castagner, Coupvray, France

[21] Appl. No.: 08/785,409

[22] Filed: Jan. 23, 1997

Related U.S. Application Data

[63] Continuation of application No. PCT/FR95/00998, Jul. 25, 1995.

[51] Int. Cl.⁶ .................................................. G01N 1/00
[52] U.S. Cl. ......................................................... 73/864.45
[58] Field of Search .................................. 73/81, 82, 84, 73/864.45, 12.08, 12.09; 173/13, 200; 89/162, 178

[56] References Cited

U.S. PATENT DOCUMENTS

| | | |
|---|---|---|
| 918,380 | 4/1909 | Schwarzlose . |
| 3,732,725 | 5/1973 | Allen, Jr. et al. ........................... 73/85 |
| 4,594,885 | 6/1986 | Rodger ................................. 73/864.45 |

FOREIGN PATENT DOCUMENTS

| | | |
|---|---|---|
| 039 654 | 11/1981 | European Pat. Off. . |
| 389 375 | 9/1990 | European Pat. Off. . |
| 2 407 296 | 5/1979 | France . |
| WO 92/10753 | 6/1992 | WIPO . |

*Primary Examiner*—Robert Raevis
*Attorney, Agent, or Firm*—Merchant, Gould, Smith, Edell, Welter & Schmidt

[57] ABSTRACT

A pyrotechnic firing device for tools connected to a firing plunger movably mounted in a launch tube. The device consists of an inner barrel or frame (1), and a firing gas generator (9) housed in a modular breech (7) at one end of the launch tube (5) secured to a weight (3) which receives the recoil on the breech (7) during firing and is connected to one end of a damping cylinder (6) between the frame (1) and the weight (3). The device is useful as an easily adaptable and convertible firing device capable of being fitted with a wide variety of tools.

7 Claims, 7 Drawing Sheets

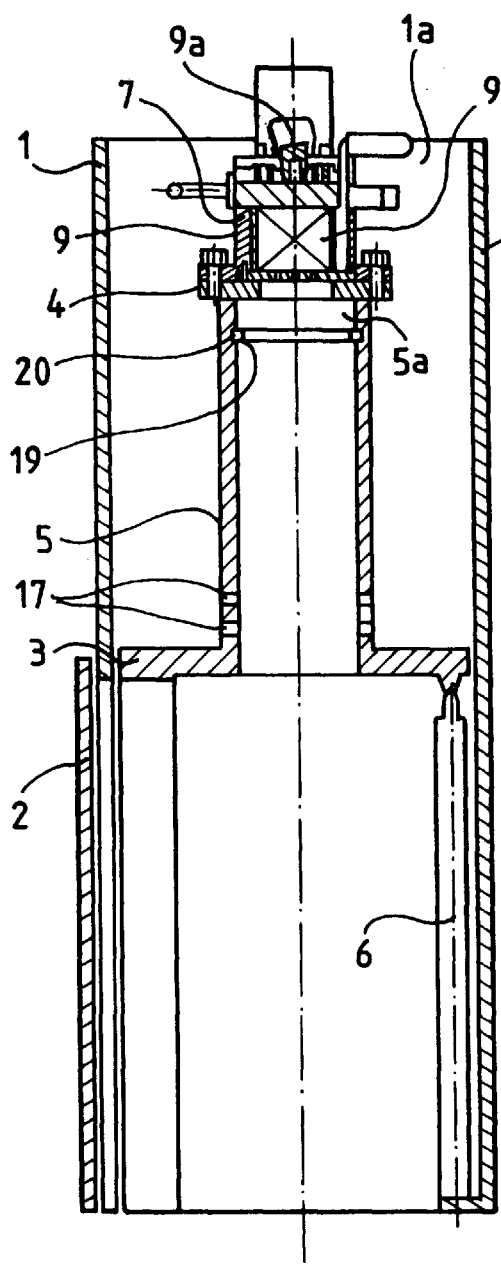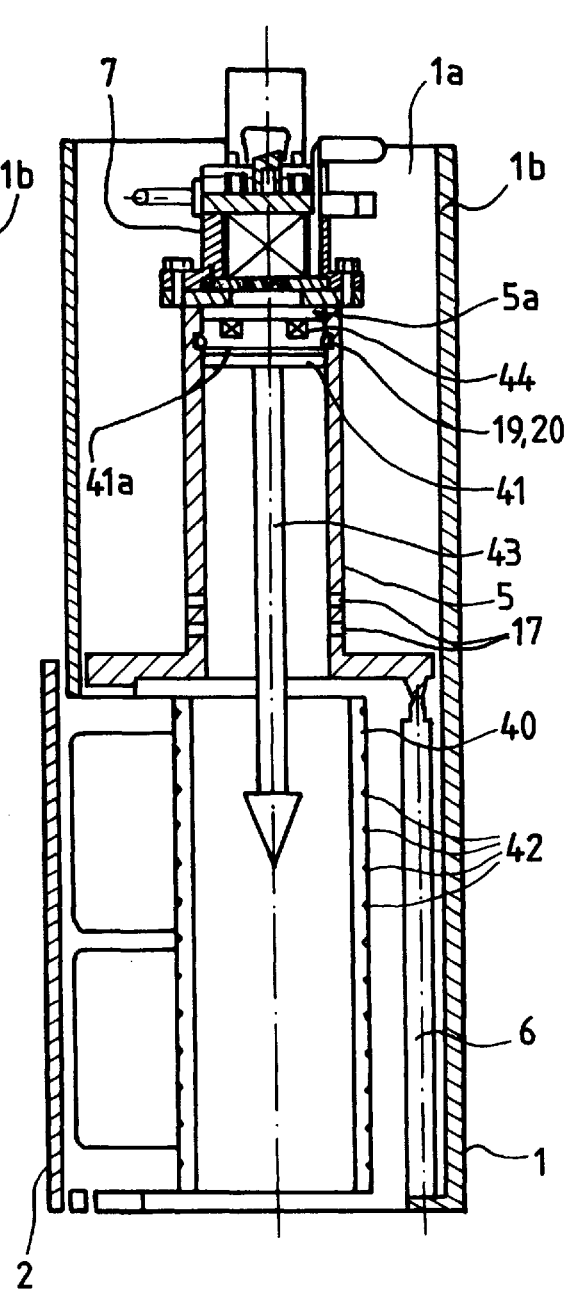

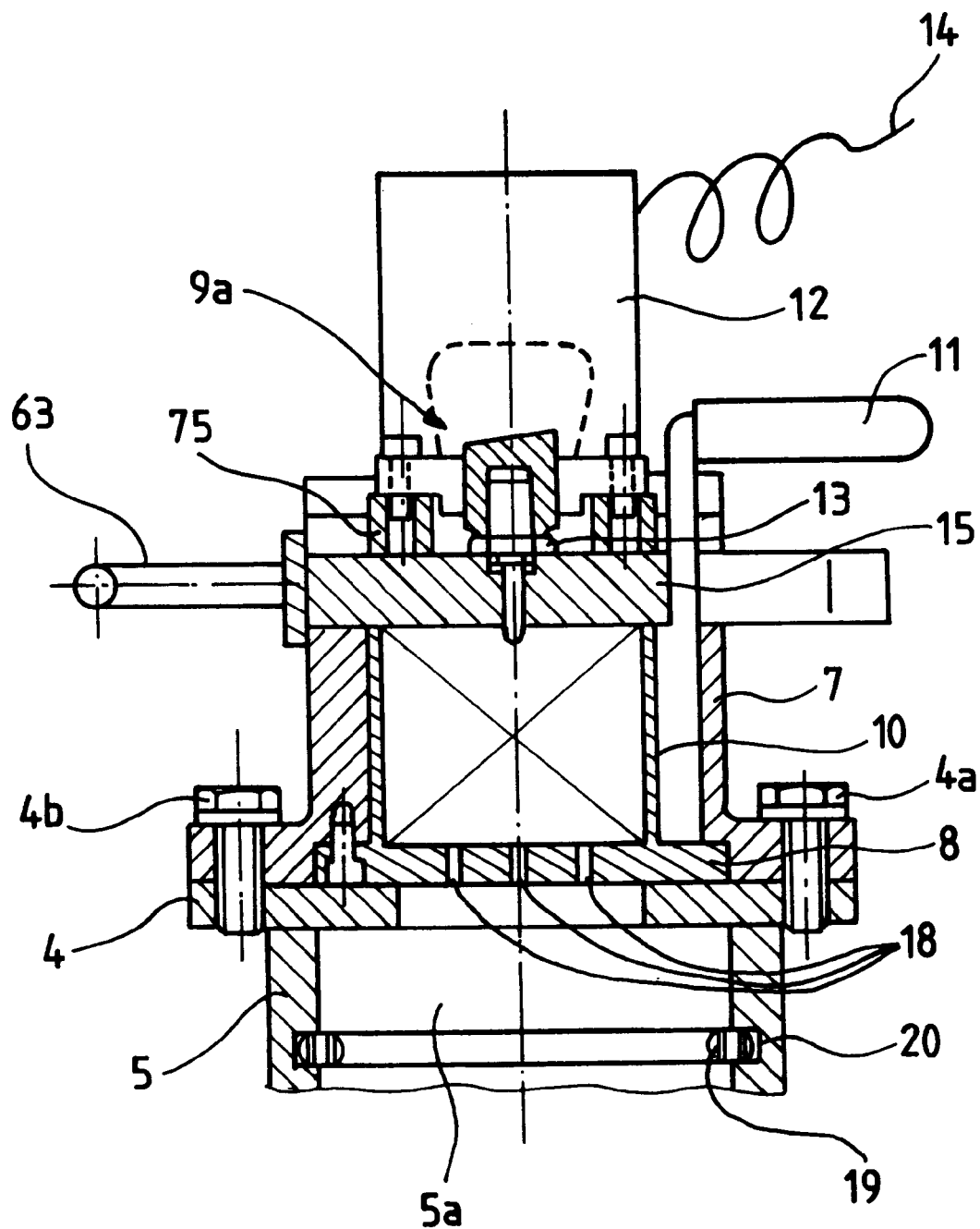
FIG_2

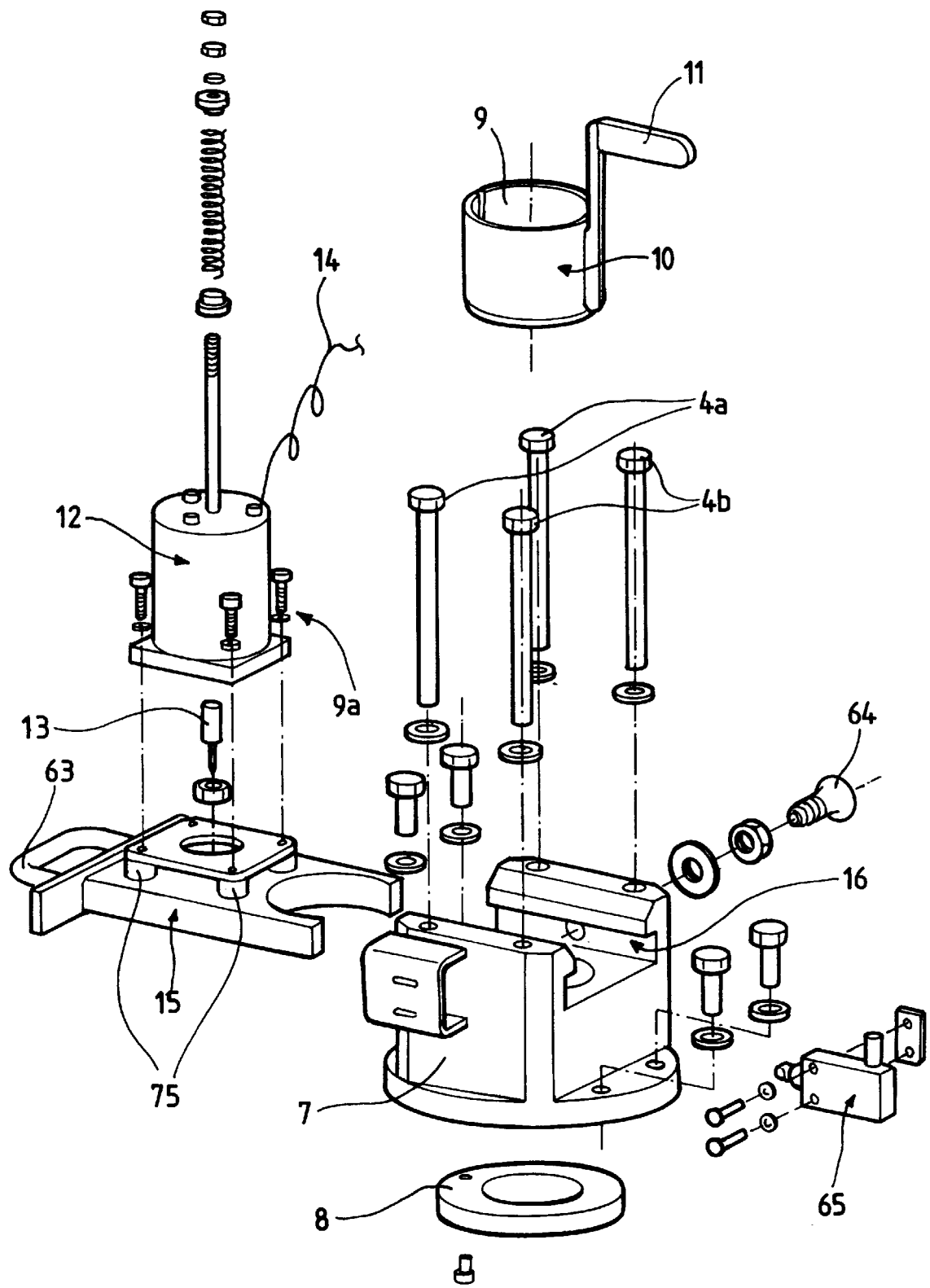
FIG_3

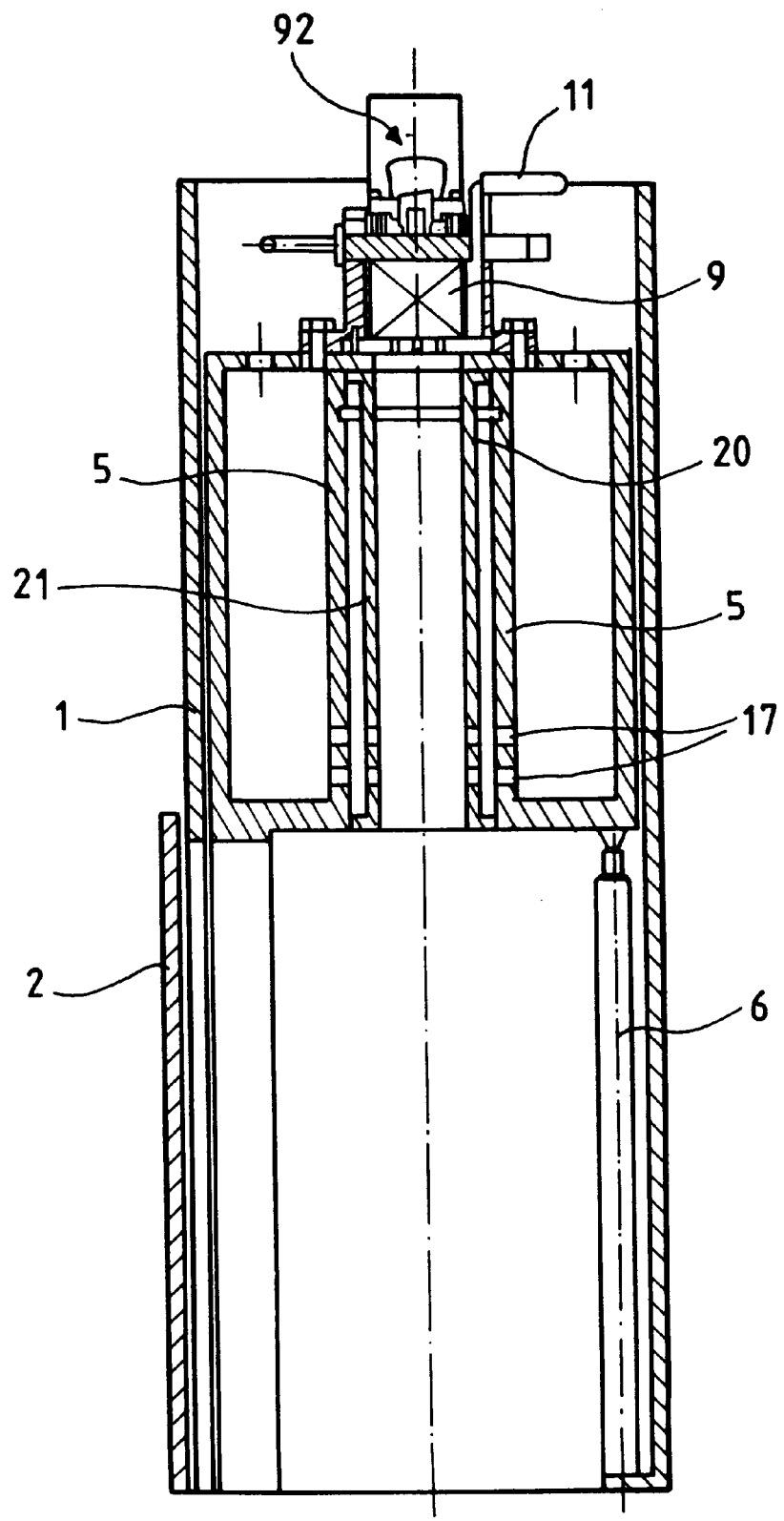
FIG_5

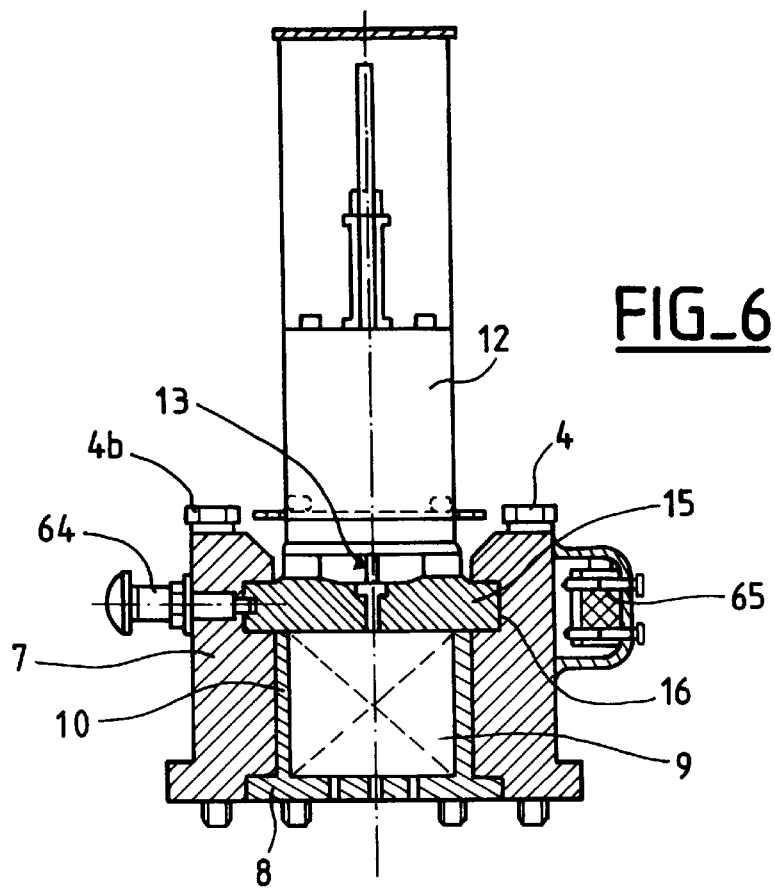
FIG_6
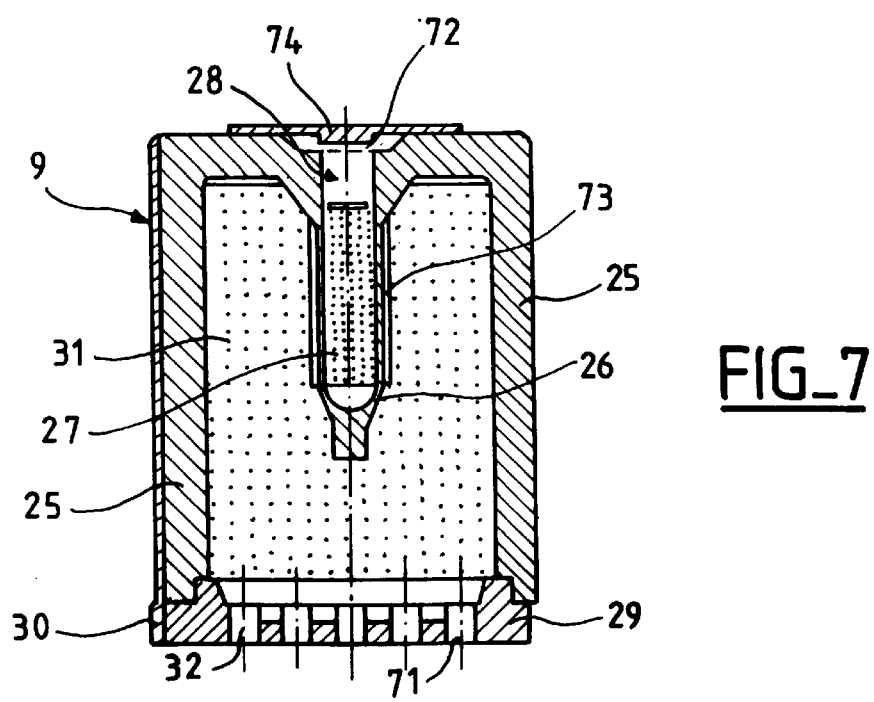
FIG_7

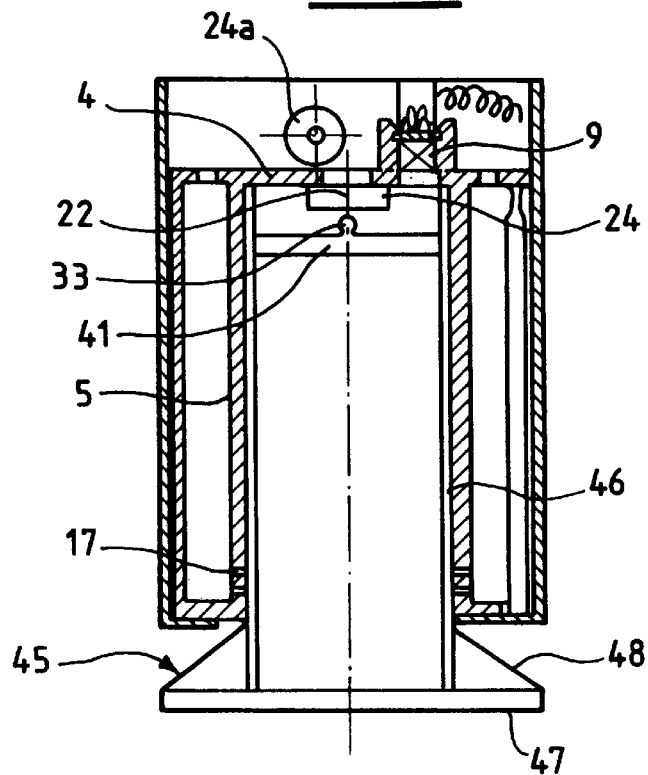
FIG_8
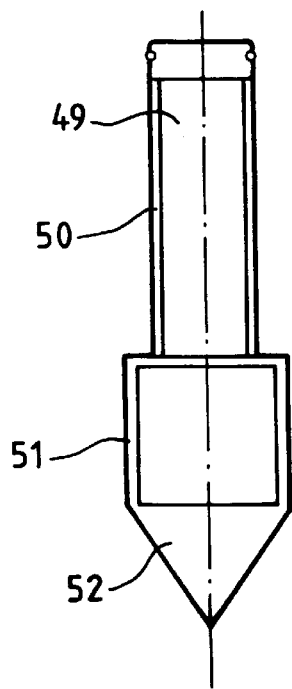
FIG_9
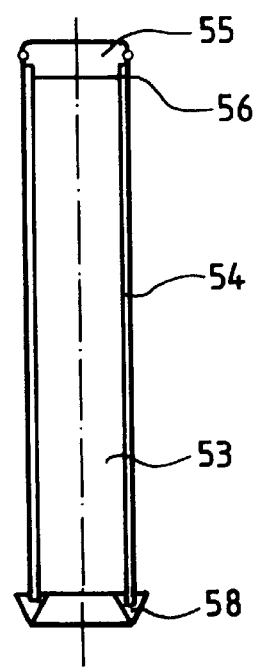
FIG_10

FIG_11 FIG_12 FIG_13
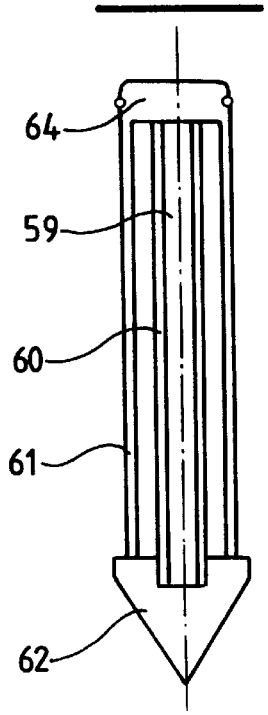
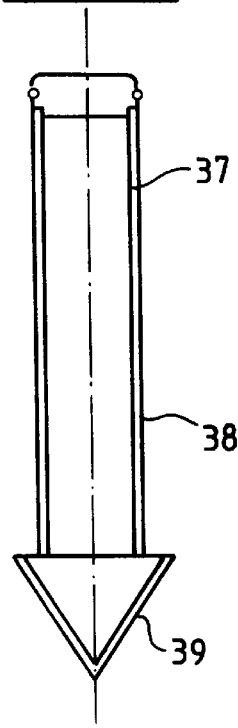
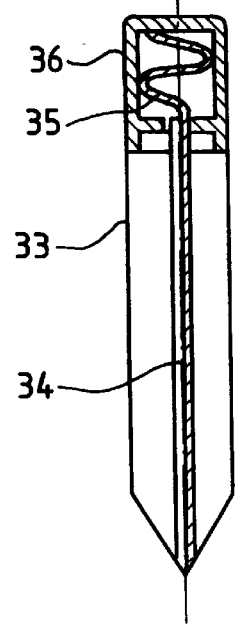
FIG_14
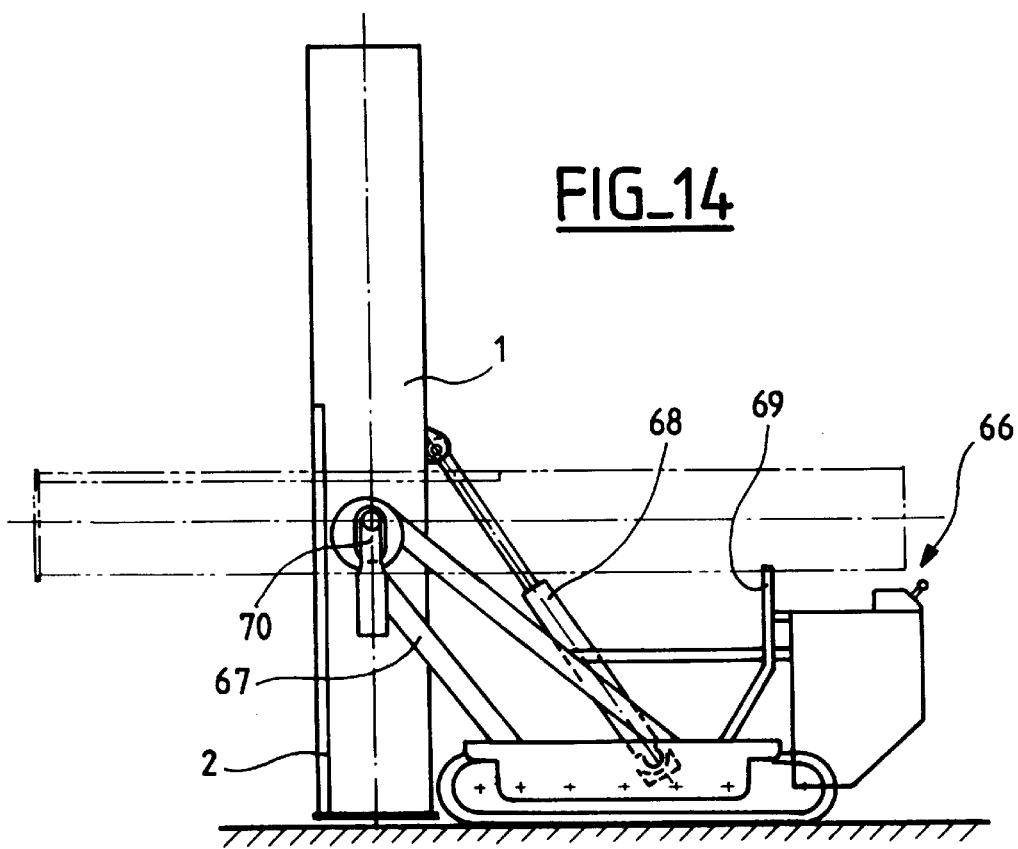

PYROTECHNIC TOOL DRIVING DEVICE

This is a continuation of PCT/FR95/00998, filed Jul. 25, 1995.

FIELD OF THE INVENTION

The present invention relates to a pyrotechnic tool driving device in which the tools are linked to a driving piston able to move inside a launching tube. Such a pyrotechnic tool driving device is part of a modular pyrotechnic tool driving system employing power supplied by a combustion gas generator and in which the recoil force is counteracted by the effect of gravity on the launching structure. The invention applies particularly to pyrotechnic tool driving equipment fitted with an intermediate piston for driving tools at high speed from a launching tube in which a combustion pressure is set up by the gases issuing from a gas generator, produced by a propulsive powder.

BACKGROUND OF THE INVENTION

EP-A-389,375 discloses a system for driving anchors into the ground using the power supplied by a gas generator, in which the recoil is counteracted by the gravitational force acting on the launching structure, the latter also acting on acoustic damping means.

Additionally, EP-A-561,968 discloses a system for measuring soil characteristics by driving a probe into the soil, the initial speed of which is obtained through the power supplied by a gas generator, and in which variations in the speed of soil penetration are measured continuously by electromagnetic coupling means.

Following successful implementation of anchor driving systems and soil characteristic measurement systems, other needs arose as expressed by various branches of civil engineering and public works, in particular relating to the compacting of surfaces, geological core sampling, localized digging of foundations etc. The expression of these needs showed there was a requirement to further improve the mechanical design, adaptability, gas generator design, and the modularity thereof, in order to reduce nuisance due to gases resulting from combustion, to improve the means allowing the launching structure to return after recoil and the damping thereof, as well as the means used to load heavy tools, while still being able to fit such systems with units for measuring soil penetration speed.

SUMMARY OF THE INVENTION

The pyrotechnic driving device according to this invention specifically sets out to better meet the requirements of users.

This is achieved, according to the invention, by a pyrotechnic tool driving device contained inside a barrel or frame, and comprises a propulsive gas generator, associated with an igniter system, situated inside a breech fixed to one end of a launching tube rigidly fixed to a ballasting mass designed to counteract a recoil force exercised on said chamber during firing, and which is linked at one of its ends to damping cylinder means inserted between said frame and said ballasting mass, for damping the fall of said ballasting mass after recoil.

In a preferred embodiment, the propulsive gas generator and igniter system for said gas generator are located externally and at one end of said launching tube, a tool being introduced into said launching tube through the other end thereof.

In another preferred embodiment, the launching tube carries, at the end thereof remote from said gas generator, venting holes for gas ejection prior to complete exit of a driving piston on said tool from said launching tube, and the venting passages discharge into an annular chamber provided between an outer wall of said launching tube and a cylindrical extension of said frame surrounding said launching tube.

According to another preferred feature, the launching tube is internally fitted with a matching tube of smaller internal dimensions, enabling pistons of tools of smaller diameter to be employed.

In a further embodiment of the invention, the gas generator igniter device preferably operates by percussion by striking an igniting charge. The igniter device is separated from the breech receiving the gas generator by a vented part designed to eject gases arising from leakage at percussion orifice level; this prevents the igniter system from becoming clogged up.

In one preferred embodiment, the device includes a tool loading unit, said unit comprising a cable passing axially through said launching tube and linked to a grasping clamp able to be released under the effect of a propulsive force acting on a piston driving a tool inside said launching tube and a sealing plate acting as an abutment member limiting upward movement of said tool within said launching tube, and controlling the release of said clamp.

The driving piston is designed to be rigidly linked to various tools such as a flat plate compactor, a spiked compactor, a core section sampling tube, a tube for burying objects in the earth, an injector, a penetration-measuring device, and an earthing or grounding cable driving rod.

Generally speaking, and with a view to reliability and safety, the gas generator is situated inside a combustion chamber and its firing or triggering system is preferably situated externally of the launching tube and away from the projected tool, or the driving piston of said tool.

The presence of a modular charge housing makes it possible to employ gas generators of differing diameters and consequently of different propulsive power weights or volumes, adapted to the power needed for correct operation of each tool. The manually-manipulated handle of the modular charge housing facilitates introduction of the gas generator, and in particular, its extraction after it has operated, from the combustion chamber. The internal diameter of the launching tube can be adapted to the diameter of the tool that is to be driven or to the diameter of a tool carrier for said tool by introducing and locking in place smaller diameter tubes inside the main launching tube.

In order to limit nuisance particularly related to the production of noise, and to possible projections of top soil etc. and excessive force on the door or gate used to close off the driving device, the launching tube is provided with lateral venting passages which make it possible, after the piston of a tool has travelled along the launching tube, to eject combustion gases upwardly into an annular chamber constituting a silencer inside the frame of the device of the invention.

The launching tube and its ballasting structure, or ballasting mass, are free to recoil vertically upwards, said recoil, counteracted by the effect of the force of gravity, corresponding to the impetus applied to the piston and to the tool thus projected or driven.

The return fall of the launching tube and its ballasting structure after tool firing is damped or shock-absorbed by a synchronized pneumatic damping cylinder which expands when the launching tube recoils thus accompanying it to the peak of its vertical trajectory and braking its fall by controlled transfer of gas between the two chambers of the gas or pneumatic damping cylinder.

Matching between the speed of upward movement of the damping cylinder, the restraining force applied to the launching tube and its ballasting structure and the speed of descent of the launching tube and its ballasting structure is achieved by means of calibrated simple or dual passages and by the inflation pressure of the damping cylinder.

In order to avoid the possibility of products of combustion from the igniter or triggering system or, possibly gases issuing from the gas generator, progressively plugging or blocking up the percussion system, the igniter or firing system, is preferably mounted on a set of slightly raised studs or supports enabling gases leaving the igniter or firing system and, if needs be, escaping gas from the combustion chamber, to be discharged from the system through the gaps between the studs, an elastic sealing membrane providing final protection of the percussion system.

Heavy tools are loaded or fitted into place, according to the invention, using a cable which passes axially through the launching tube. Driving devices for driving heavy tools are fitted with an off-center combustion chamber to allow passage of the cable which preferably is wound onto a drum by means of an electric motor. The cable carries a clamp at one end, said clamp being releasable either mechanically due to a pulling force created by gas pressure, or electrically, or again, by the effect of the pressure inside the launching tube.

The pyrotechnic tool driving device according to the invention can be fitted with a tool projection speed measuring tube. This is achieved by inserting a composite measuring tube onto a rigid non-magnetic non-conducting composite material structure, in order to thus link the measuring tube to the device frame. The pyrotechnic tool driving system thus provided is preferably mounted on a tracked transporting unit, but, in the case of smaller units, it can be transported on a carrier which may or may not be motor-driven, or carried at the back of a truck or small lorry, or even on a railway wagon. According to the invention, a quick-acting fastening system for fixing the device on a public works vehicles such as a mechanical excavator enables the pyrotechnic tool driving system to be used as a tool that can be interchanged with the buckets of the excavator.

The pyrotechnic driving system can thus be loaded either vertically or horizontally. Bringing it to the folded position for loading or for transport is preferably achieved by means of a mechanical system using a gear wheel and an endless screw driven by an electric motor. Nevertheless, other motion-imparting systems can be applied, such as hydraulic jack-type systems and hydraulic motors, gears and transmission belts. Further aims, features and advantages will become more clear from the description that follows of various embodiments of the invention, provided by way of non-limiting example and with reference to the attached drawings.

BRIEF DESCRIPTION OF THE DRAWINGS

FIG. 1 shows a pyrotechnic tool driving device according to the invention in longitudinal cross-section.

FIG. 2 shows a longitudinal cross-sectional view on a larger scale of a combustion chamber sub-assembly which is associated to the pyrotechnic tool driving device according to the invention.

FIG. 3 is an exploded view of the combustion chamber sub-assembly shown in FIG. 2.

FIG. 4 is a longitudinal cross-sectional view of another embodiment of a pyrotechnic tool driving device according to the invention, in which a tool consisting of a rodlike probe cooperates with a system for measuring penetration speed.

FIG. 5 is a view in longitudinal cross-section of another embodiment of the pyrotechnic tool driving device according to the invention in which a tube for reducing the cross-sectional diameter thereof has been mounted inside the launching tube.

FIG. 6 is an axial cross-section of another embodiment of a combustion chamber sub-assembly of the pyrotechnic projection device according to the invention.

FIG. 7 is a cross-sectional view taken at the level of the igniter or firing device, of the gas generator used in the pyrotechnic driving device according to the invention.

FIG. 8 is a longitudinal cross-section of another embodiment of the pyrotechnic tool driving device according to the invention, in which the tool is being fitted with the help of an axial loading cable.

FIGS. 9 to 13 show various embodiments of tools able to be associated with the pyrotechnic driving device according to the invention.

FIG. 14 is an elevational view of a tracked vehicle for transport and placement of a tool driving system using the pyrotechnic driving device of the invention.

DETAILED DESCRIPTION OF THE PREFERRED EMBODIMENTS

With reference now to FIG. 1, it can be seen that the pyrotechnic tool projection or driving device according to the invention is mounted inside a frame or barrel 1 of a generally cylindrical shape fitted with an access door or gate 2 giving access to the portion thereof where said tool is fitted in place for firing. The launching structure mounted inside frame 1 includes a ballasting mass 3 the purpose of which is to guide the launching structure inside the frame during recoil and return of said structure, the base or end plate 4 of an expansion chamber, and the launching tube 5.

A damping device (in the present case a pneumatic damping cylinder) 6, fitted between frame 1 and ballasting mass 3, is caused to expand when the launching structure recoils in order to then act as a damper when the structure redescends.

In FIGS. 2, 3 and 6, the combustion or propulsion breech unit receiving a gas generator or propulsive cartridge 9 consists of a burst-resistant chamber 7, a plate 8 provided with discharge orifices 18 for combustion gases, and an enclosure forming a loading housing 10. The breech 7 is rigidly, and releasably—using for example bolts 4a and 4b—fixed onto the base 4 of the expansion chamber 5a further defined by the inner wall of launching tube 5. The modular structure of chamber 7 thus fitted externally and releasably onto launching tube 5 simultaneously allows different launching tubes and different gas generators (propulsive charges) 9 to be employed which can be readily introduced into and extracted from breech 7 with the help of a handle 11 of a suitable shape to be grasped manually.

The operation of the pyrotechnic tool driving device according to the invention will now be described with reference to FIGS. 1 to 4. Having set up the launching tube 1 vertically at the "firing" position, for example using the tracked vehicle shown in FIG. 14, the tool which is to be driven, for example the penetration measuring instrument 43 illustrated in FIG. 4 is fitted into the launching tube through the door or gate 2. Piston 41 of the tool slides along the launching tube 5 towards baseplate 4 until the resilient ring 19 carried by the launching tube 5 simultaneously engages into an annular groove 41a of piston 41 of the tool and into a groove 20 of tube 5.

In order to load the propulsive charge into breech 7, cover 15 is slid out, so that the propulsive charge 9, surrounded by its loading housing 10 can be inserted into the receiving enclosure 9a of breech 7 holding it by means of handle 11, and then, after cover 15 has been refitted rigidly locking the propulsive charge in position with its igniter 26 (see FIG. 7) opposite striker plate 13.

After possibly once more checking that the launching tube 5 is perfectly vertical, or that the tool is correctly oriented with respect to the desired line of fire, and after ensuring that the persons working on the site are well clear, firing can proceed which is done by, for example, turning a key in a firing controller. Propulsive charge 31 is ignited by the primer 28 and firing powder 27 and undergoes rapid combustion generating an extremely high pressure in chamber 5a of launching tube 5. The effect of this pressure is to drive piston 41 and the tool united therewith downwards at high speed accompanied by an upward recoil of breech 7, launching tube 5 and of the ballasting mass 3 associated therewith. The tool, for example penetration measuring tool or penetrometer 43 is driven into the ground while the assembly comprising launching tube and ballasting mass 3 are projected upwardly through a distance of typically several tens of centimeters, while being braked by the effect of gravity; they return to the inactive or rest position aided by pneumatic damping cylinder 6.

Gases produced by the propulsive charge 9 partially escape into the annular space 1a after piston 41 has travelled beyond venting passages 17 (see FIGS. 1, 4 and 5), and partially are projected downwards following piston 41 and continuing to propel the latter for several centimeters.

The pyrotechnic tool driving device can then be moved to the position where it is required to "fire" the next tool, which may optionally be a tool of a different type, or which may optionally involve the use of a different diameter launching tube or a different power propulsive charge.

As can be seen in FIGS. 1, 4 and 5, launching tube 5 has an internal annular groove 20 close to its upper closed end 4 but sufficiently spaced therefrom to accommodate piston 41, into which a circular- or polygonal-section resilient ring 19 is mounted for tightly surrounding and blocking the piston of the tool to be ejected (also see FIG. 2).

Smaller diameter launching tubes 21 (shown in FIG. 5) designed to project smaller diameter tools or tool carriers may be fitted into the main launching tube 5.

The igniter system 9a for triggering explosion of propulsive charge 9 preferably employs percussion using an electromagnet 12 fitted with a fixed or adjustable striking plate 13. The electromagnet 12 is connected to a source of power by an extendible spiral lead 14. The electromagnet can be replaced by some other percussive-action triggering device such as a pneumatic cylinder, a combination of a hydraulic cylinder and spring means, a manually-stretched spring, or an electric motor. Where the propulsive charge cartridge is ignited by laser energy or electrically, the electromagnet is replaced by a laser source or, respectively, by an electric igniter designed to be connected to a source of power such as a battery. A sliding cover 15 (see FIG. 3) carrying the striking plate 13 closes off the top of chamber 7, this being achieved, for example, by simply sliding it in grooves 16. Breech 7 also constitutes a rigid interchangeable subassembly designed to be fitted externally and in a releasable fashion at one end (end plate 4) of launching tube 5.

Venting passages 17 provided in the launching tube 5 close to the end thereof remote from the propulsive charge 9, allow the propulsion gas to escape upwardly, before the piston 41 of the tool completely leaves the launching tube 5. The venting passages 17 discharge into an annular chamber 1a which is principally defined between a cylindrical extension 1b of frame 1 and the outer wall of launching tube 5. An exhaust pipe arrangement allowing propulsion gases to exhaust upwardly is thus obtained, making it possible to eliminate or at least reduce significantly nuisance possibly arising through the noise produced by the pyrotechnic driving device when it operates, and possible projections of pieces of top soil or the surface being driven into.

The gas generator shown in FIG. 7 consists of a housing 25 which is preferably made of a composite material such as a thermoplastic or thermosetting resin which may or may not be reinforced with carbon fibers, or other materials. The said housing includes an encased ignition initiating means 26 enclosing ignition powder 27 and a primer 28 and percussion striker which is triggered electrically or by laser. The housing 25 contains the actual propulsive powder 31 which, once ignited, generates, by sudden combustion, the gases for driving piston 41 of the tool. A positioning lug 30 ensures that the gas generator contained in housing aiding loading 10 is correctly fitted into breech 7.

In one design of gas generator, a cover 29 has varying numbers of pre-weakened thin walled zones 32 which after shearing through orifices 18 provided in plate 8, allow controlled passage of combustion gases, as a function of the quantity of propulsive powder 31.

These orifices are closed off by a cover strip 71. A sealing gasket 72 ensures the primer is protected from possible ingress of moisture. The primer is kept in place by a small tongue 73 formed by molding. An adhesive rigid foam plug or washer 74 protects the primer from accidental shock.

In one embodiment of the invention (see FIG. 8), a cable 22 designed to load heavy tools carries a releasable clamp 23 and an abutment plate 24. In order to raise the tool, this cable is for example wound onto pulley 24a for example driven by an electric motor. Where clamp 23 is of a type able to be mechanically released due to the pulling force exercised by the tool on the cable, operation is as follows: the pressure generated in launching tube 5 keeps plate 24 firmly pressed against the base or end plate 4 of launching tube 5 and, while exercising a powerful downward force on piston 41 of the tool, pulls on cable 22 retained by plate 24 thus causing clamp 23 to release. This clamp can also be provided with a pressure-sensitive opening system which is responsive to gas pressure inside launching tube 5.

According to the invention, the pyrotechnic tool driving device can be fitted with a measurement tube 40 for monitoring changes in the speed of the tool. The piston 41 (see also FIG. 4) of said tool is then fitted with a magnet 44 and is rigidly connected to the measuring rod 43 of a dynamic penetrometer or penetration measuring system. Regularly spaced windings 42 are provided at different levels on measuring tube 40 to allow, preferably via a cathode ray tube oscillograph or display, the travel of magnet 44 with respect to time to be monitored.

The relative positions of the door or gate 2 and its rotary hinge covering the opening in the firing tube make it possible, when door or gate 2 is open, to remove the split measuring rod of a rodlike probe, or of a tool which has failed to be driven in completely.

The pyrotechnic driving device of this invention can be fitted with a large range of tools. In the embodiment shown in FIG. 8, a flat plate 45 compacting tool has been shown. This tool consists of a tube 46, slidable into launching tube 5, and which is closed at its upper end and carrying a compacting plate 47 reinforced by stiffeners 48 at its lower end, the said plate being able to be circular or polygonal in shape. Such a tool is useful for compacting earth and particularly trenches and infill. The significant power that is communicated to the tool by the gas generator, enables highly effective and rapid compacting to be achieved.

The pyrotechnic tool driving device may be fitted with a spiked compacting tool 49 illustrated in FIG. 9. Such a device consists of a tube 50 slidable into launching tube 5 and extended by a compacting tube 51 which is preferably cylindrical and of the same or a different diameter, ending in a point or spike 52 aiding penetration. The compacting tube, or its point of spike, may have a flat bottom. This type of tool is used for providing holes having compacted walls. When providing localized foundations in concrete, the load carrying capacity of the concrete posts is significantly improved, for a given foundation volume, by the presence of such compacted-wall holes.

In another embodiment, the pyrotechnic propulsion device can be fitted with a tube for taking core samples 53 shown in FIG. 10. Such a tool consists of a tube 54 slidable into launching tube 5 and closed at its upper end by a closing member 55 with fast-acting closing means 56, opening thereof allowing the core sample to be ejected. The tube 54 is preferably extended by the core sampling tube but a tube of a different diameter can be used to extend the tube 54 in order to provide core samples of a diameter different from that of the tube 54. The core sampling tube is terminated by means of a cutting section (not shown) or by a projecting knife 58. Without departing from the scope of the invention, it can be fitted with various systems to enable the core section to be cut, as used in standard geological core section sampling tubes. Such a tool is used for obtaining core sections for soil analysis or for providing holes which are preferably cylindrical, after a core section has been removed from the ground.

The pyrotechnic tool driving device can be fitted with a tube designed to bury an explosive or propulsive charge 59, shown in FIG. 11. Such a tube 59 is fitted with a preferably hollow rod 60 which is closed at its upper end and surrounded by a tube 61 which is preferably made of a plastics material or cardboard or the like, and being terminated by a conical tip 62 for aiding penetration, this tip preferably having a projecting section. After the conical tip has penetrated the ground, tube 60 is removed. Outer tube 61 together with the conical tip remain in the ground. A pyrotechnic charge can be introduced into the channel thus left free following extraction of rod 60. The channel thus created can be used to bury other elements, materials or items of equipment apart from pyrotechnic charges.

In order to illustrate applications able to be carried out using the pyrotechnic tool driving devices of the invention, a pyrotechnic driving device designed to drive a hollow rod 37 closed at its lower end 39 and provided with lateral openings 38 into a road surface is illustrated in FIG. 12. Such a tool can be used, once it has been driven into a road surface, as a channel for injecting resin or a sealing cement-like compound, or for introducing cables or superstructures.

The pyrotechnic tool driving device can be equipped with a rodlike tool 33 for an earthing or grounding cable 34. Such a tool enables the cable to be buried, the guide rod preferably having an L- or T-shaped profile, other profiles being however possible. The excessive length of grounding cable 35 is preferably coiled inside the head of piston 36.

The pyrotechnic tool driving device according to the invention can be used to project tools able to be recovered, or designed to remain in the ground, into materials or structures such as walls, concrete platforms, highway or road surfaces, etc.

The subassembly constituted by gas generator 9 and its igniter system 9a as illustrated in FIG. 6 is fastened in a readily removable fashion to the breech 7 which, in its turn, is fixed by means of bolts 4a, 4b to the base or end plate 4 (not shown) of launching tube 5. The igniter system 9a is secured to closing plate 15, and isolated therefrom by four studs 75 forming a venting system for evacuating gases from the firing system. It can be seen, in conjunction with the exploded view in FIG. 3, how the slidable closing plate 15 that can be slid in the two slideways 16 of breech 7 with the aid of handle 63, is locked in position prior to and during firing by a tabbed safety screw 64. A safety sensor 65 ensures that the plate 15 carrying electromagnet 12 is properly mounted and locked in position (by releasing tabbed safety screw 64) before firing can be actuated by electromagnet 12 acting on striking plate 13.

On FIG. 14, a transporting vehicle 66 for transporting and locating the tool driving device according to the invention is shown. The transporting vehicle 66 includes a connecting structure 67 for the frame 1 of the tool driving device, jacking means 68 for rotating the frame 1 suitably for transport and firing, and a skew correcting jack 69, and a rotation head 70.

Obviously, this invention is not limited to the embodiments that have been described and shown in the drawings but may be subject to numerous variations available to those skilled in the art without departing from the scope of the invention as defined herein.

We claim:

1. A pyrotechnic tool driving device linked to a driving piston movable inside a launching tube, wherein said pyrotechnic tool driving device is contained inside a barrel or frame (1), and comprises a propulsive gas generator (9), associated with an igniter system (9a), situated inside a breech (7) fixed to one end of said launching tube (5) rigidly fixed to a ballasting mass (3) which counteracts a recoil force exercised on said breech (7) during firing, said ballasting mass being linked at one of its ends to damping cylinder means (6) inserted between said barrel or frame (1) and said ballasting mass (3), for damping the fall of said ballasting mass after recoil.

2. A pyrotechnic tool driving device according to claim 1, wherein said propulsive gas generator (9) and said igniter system (9a) for said gas generator constitute subassemblies which are mounted externally to said launching tube and which are easy to remove, said subassemblies being fixed to said breech (7) at one end of said launching tube (5), a tool being introduced into said launching tube through the other end thereof.

3. A pyrotechnic tool driving device according to claim 1, wherein said launching tube (5) carries, at the end thereof remote from said gas generator (9), lateral venting holes (17) for gas ejection prior to complete exit of said driving piston (41) from said launching tube (5), and wherein said venting passages discharge into an annular chamber (1a) provided between an outer wall of said launching tube (5) and a cylindrical extension (1a) of said frame (1) surrounding said launching tube (5).

4. A pyrotechnic tool driving device according to claim 1, characterized in that said launching tube (5) is internally fitted with a matching tube (21) of smaller internal dimensions, enabling pistons (41) of tools of smaller diameter to be employed.

5. A pyrotechnic tool driving device according to claim 1, characterized in that said igniter device (9a) operates by percussion by striking a primer (28) of an ignition gas generator, said igniter device being separate from said chamber (7) receiving said gas generator (9) and being isolated therefrom by a vented part (75) adapted to eject gases formed by combustion of said igniting charge.

6. A pyrotechnic tool driving device according to claim 1, wherein said pyrotechnic tool driving device includes a tool loading unit, said unit comprising a cable (22) passing axially through said launching tube (5) and linked to a grasping clamp (23) able to be released under the effect of the propulsive force acting on a piston (41) driving a tool inside said launching tube (5) and a sealing plate (24) acting as an abutment member limiting upward movement of said tool within said launching tube (5), and upon controlled release of said clamp (23).

7. A pyrotechnic tool driving device according to claim 1, wherein said tool is one among the following tools: a flat plate compactor (45), a spiked compactor (49), a core section sampling tube (53), a tube for burying objects in the earth (59), an injector (37), a penetration-measuring device (43), and an earthing or grounding cable rod (33).

* * * * *